United States Patent [19]  
Iacobucci et al.

[11] 4,105,675  
[45] Aug. 8, 1978

[54] METHOD FOR MAKING 3-DEOXYANTHOCYANIDINS

[75] Inventors: Guillermo A. Iacobucci; James G. Sweeny, both of Atlanta, Ga.

[73] Assignee: The Coca-Cola Company, Atlanta, Ga.

[21] Appl. No.: 662,742

[22] Filed: Mar. 1, 1976

[51] Int. Cl.$^2$ .................... C07D 311/60; A23L 1/275
[52] U.S. Cl. ............................ 260/345.2; 260/345.5; 426/250; 426/268; 426/540
[58] Field of Search ................. 260/345.2, 345.5

[56] References Cited

U.S. PATENT DOCUMENTS 3,266,903  8/1966  Jurd ...................................... 426/177

OTHER PUBLICATIONS

Bell, Aust. J. Chem., 22, 601 (1969).
Clark-Lewis et al., Aust. J. Chem., 21, 2247 (1968). 4n 30 McLoughlin, Chem. Comm., pp. 540–541 (1969).

*Primary Examiner*—Nicky Chan
*Attorney, Agent, or Firm*—Michael J. Gilroy; Robert A. Lester; John R. Martin

[57] ABSTRACT

Method for preparing a 3-deoxy-5-hydroxyanthocyanidin salt having a 4' and/or 7 OH substituent from a corresponding acylated flavanone, by (1) reducing the acylated flavanone in a solvent medium by reaction with an alkali borohydride to form a corresponding flavan not having an OH substituent at the 4 position, and (2) oxidizing the flavan or an acylated or hydrolyzed derivative of the flavan in an organic solvent medium by reaction with a halogenated benzoquinone in the presence of a strong acid and water. Suitable acylated flavanones include acetylated natural flavanones, especially acetylated naringenin and hesperetin.

56 Claims, No Drawings

METHOD FOR MAKING 3-DEOXYANTHOCYANIDINS

BACKGROUND OF THE INVENTION

1. Field of the Invention

This invention, in general, relates to heterocyclic carbon compounds including a carbocyclic nucleus fused to a 6-membered ring containing one heterooxygen atom and, in particular, to a process for converting acylated flavanones to 3-deoxyanthocyanidins.

2. Description of the Prior Art

Anthocyanins are a family of plant pigments widely occurring in nature which are responsible for the yellow, red and purple hues of most flowers and fruits. The term "anthocyanin" chemically designates a substituted flavylium (or 2-phenylbenzo-pyrylium) salt, the cation of which has the structure:

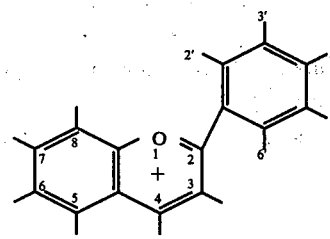

the substitutents at the 3-8 and 2'-6' positions in the case of known naturally occurring anthocyanins denoting either H, OH, OCH$_3$ or O-sugars. The latter, corresponding to monosides, biosides and triosides usually containing glucose, galactose, rhamnose, arabinose or xylose, are found almost exclusively at the 3 and 5 positions.

The term "anthocyanidin" refers to the aglycone of any anthocyanin, i.e., the substituted flavylium salt freed of all sugar components.

The color of anthocyanidins is dominated by the nature of the substituent at the 3 position. When it is H, the resulting 3-deoxyanthocyanidins have $\lambda_{max} \sim 470$ nm in water at pH 4 or lower, and give yellow solutions. The presence of an oxygenated substituent at the 3 position (OH, OCH$_3$, O-sugar) shifts the absorption spectra bathochromically, giving rise to red anthocyanidins ($\lambda_{max} \sim 530$ nm). P. Stevenson, *J. Molecular Spectroscopy*, 18, 51–58 (1965).

These pigments have been associated with the human food chain since the dawn of civilization, being consumed as part of fruits, grains and vegetables. The absence of scientific records ascribing ill-effects to the consumption of anthocyanidins as part of the regular diet makes them attractive additives for food coloration. L. Jurd, U.S. Pat. No. 3,266,903 (Aug. 16, 1966); U.S. Pat. No. 3,301,683 (Jan. 31, 1967) and U.S. Pat. No. 3,314,975 (Apr. 18, 1967); and C. F. Timberlake, Ger. Pat. No. 1,904,810 (Oct. 2, 1969).

Of the anthocyanidins, the present invention is concerned with 3-deoxyanthocyanidins and their preparation from acylated flavanones, i.e., those containing the functional group

hereinafter referred to as OCOR, especially those derived from naturally occurring flavanones. Synthesis of 3-deoxyanthocyanidins has been accomplished in the laboratory by acid-catalyzed condensation of substituted o-hydroxybenzaldehydes with appropriate acetophenones. G. M. Robinson, R. Robinson and A. R. Todd, *J. Chem. Soc.*, 809(1934), and previous papers in this series. This method is exemplified below by the synthesis of apigeninidin, a constituent of certain varieties of corn and sorghum. E. D. Styles and O. Ceska, *Phytochem.* 14,413 (1975) and W. K. Nip and E. E. Burns, *Cereal Chem.* 48, 74 (1971):

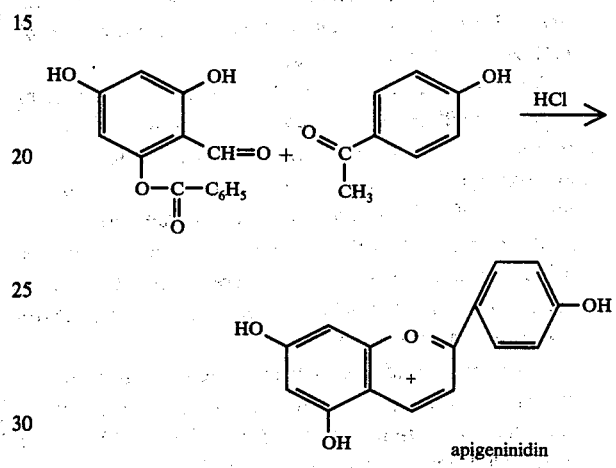

Although this method is useful in the laboratory, its industrial practice could be constrained by the availability and cost of raw materials, particularly in connection with the synthesis of naturally-occurring anthocyanidins having extensive phenolic substitution.

SUMMARY OF THE INVENTION

The present invention is directed to a method for preparing a 3-deoxyanthocyanidin salt of the formula:

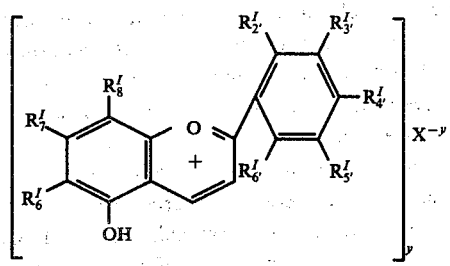

wherein $R_{6-8,3'-5'}{}^I$ are H, OH or lower alkoxy, at least one of $R_7{}^I$ and $R_4{}^I$ is OH, $R_{3'-5'}{}^I$ (and preferably $R_{6-8}{}^I$ as well) do not include vicinal OH, $R_2{}^I$ and $R_6{}^I$ are H or lower alkoxy, X is an anion, such as chloride, bromide, sulfate, phosphate, aryl and alkyl sulfonates or fluoride (preferably an anion suitable for food use, such as chloride or phosphate, especially the former), and y corresponds to the valence of the anion from an acylated, preferably acetylated, flavanone of the formula:

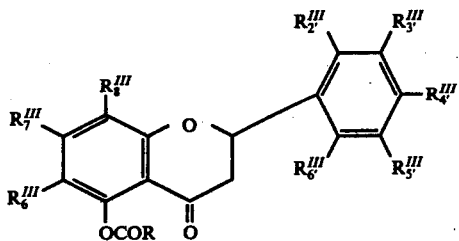

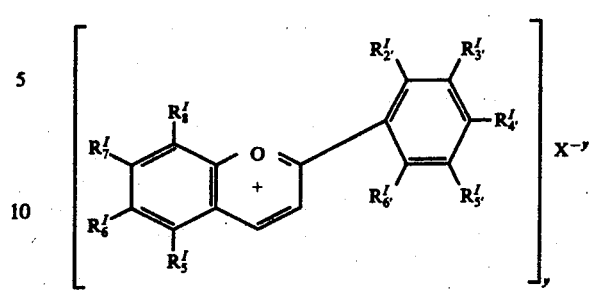

wherein $R_{6-8, 2'-6'}^{III}$ are the same as $R_{6-8,2'-6'}^{I}$ except that those $R_{6-8, 3'-5'}^{III}$ corresponding to those $R_{6-8,3'-5'}^{I}$ which are OH are, and R is lower alkyl or phenyl, preferably CH$_3$ said method comprising, (a) reducing said acylated flavanone in an organic solvent medium, preferably a solvent such as an aliphatic alcohol, alicyclic alcohol, lower aliphatic ether and/or cyclic ether, by reaction at a temperature of about 5°-50° C (preferably at room temperature for about one hour) with an alkali borohydride such as lithium, potassium and/or sodium borohydride, preferably the latter, to form a flavan not having an OH substituent at the 4 position, and (b) oxidizing said flavan or an acylated or hydrolyzed derivative thereof in a solvent medium by reaction, preferably at a temperature of about 80°-120° C. for about 0.5-2 hours, with a halogenated benzoquinone in the presence of a strong acid to form said 3-deoxyanthocyanidin salt, said solvent medium of this step and said strong acid together forming a protic medium, preferably an aqueous protic medium. In preferred embodiments, $R_{6,8,5' and/or 6'}^{I}$ are H. When $R_7^{I}$ is OH, $R_4^{I}$ most preferably is OH or lower alkoxy. Advantageously the acylated flavanone is a fully acylated flavanone of pinocembrin, naringenin, isosakuranetin, homoeriodictyol, hesperetin, citronetin or sakuranetin. In the most preferred embodiments said acylated flavanone is naringenin triacetate or hesperetin triacetate. The solvent medium of step (c) suitably is a protic organic solvent inert to the dehydrogenative action of the halogenated benzoquinone, such as a lower aliphatic monofunctional alcohol and/or carboxylic acid, especially acetic acid. Preferably, the strong acid has the formula $H_yX$ and is selected from those acids which neither react with the anthocyanidin cation nor precipitate the same in an aqueous medium, such as hydrochloric acid, hydrobromic acid, sulfuric acid, phosphoric acid and/or aryl and alkyl sulfonic acids, most efficaciously in aqueous form. Suitable halogenated benzoquinones include tetrachloro-, tetrabromo- and tetrafluoro-benzoquinones most preferably tetrachloro-p-benzoquinone and/or tetrabromo-p-benzoquinone.

Another aspect of the invention is concerned with a method for preparing a 5-hydroxyflavan intermediate by following step (a) as set forth above.

A further facet of the invention pertains to a method for preparing a 3-deoxyanthocyanidin salt of the formula:

wherein $R_{6-8,2'-6'}^{I}$, X and y are as previously described and $R_5^{I}$ is H, OH (preferably non-vicinal) or lower alkoxy (most preferably OH as previously described); said method comprising: (a) providing a corresponding flavan (II) wherein $R_5^{II}$ is OH or OCOR if $R_5^{I}$ is OH and (b) oxidizing said flavan under the conditions described above in step (c).

The present invention also deals with a flavan of the formula:

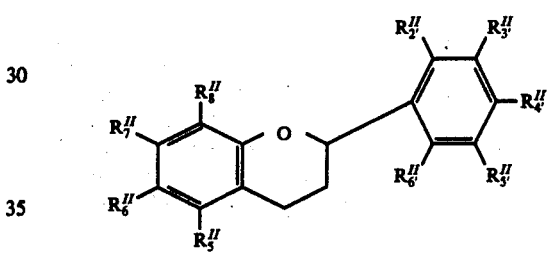

wherein $R_{6-8,3'-5'}^{II}$ are H, OH, OCOR or lower alkoxy, at least one of $R_7^{II}$ and $R_4^{II}$ is OH or OCOR, $R_{3'-5'}^{II}$ do not include vicinal OH or OCOR substituents, $R_2^{II}$ and $R_6^{II}$ are H or lower alkoxy, $R_5^{II}$ is OH or OCOR and R is lower alkyl or phenyl, preferably CH$_3$. Preferred variations are as set forth above or as resulting therefrom.

DESCRIPTION OF PREFERRED EMBODIMENTS

In seeking an alternative to prior art techniques for preparing 3-deoxyanthocyanidins the inventors have discovered a two step reduction-oxidation synthesis based on the transformation of specified acylated flavanones. Concurrently, the inventors have discovered a process for reducing acylated flavanones to flavans, a process for oxidizing flavans to 3-deoxyanthocyanidins and a family of flavans. As will become apparent hereinafter, although the latter three embodiments are integrally related to the first embodiment, they need not be of the same scope due to, e.g., variances in processing requirements and the state of the art.

The starting acylated flavanones of the invention have the generic formula:

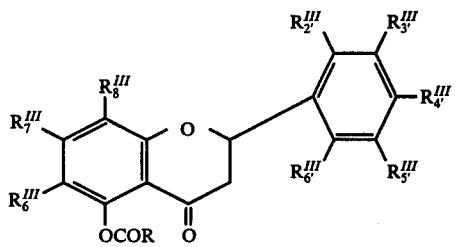

III particularly suitable. Omitted from the table are flavanones, such as eriodictyol, whose corresponding flavan intermediates do not convert to anthocyanidins because of vicinal hydroxyl or acyloxy groups, as will be discussed hereinafter. It should be noted, however, that such omitted flavanones can be effectively reduced to the flavan intermediate form and thus are suitable in the embodiment of the invention directed to the reduction of acylated flavanones.

TABLE 1

List of Selected 5-Hydroxyflavanones IV

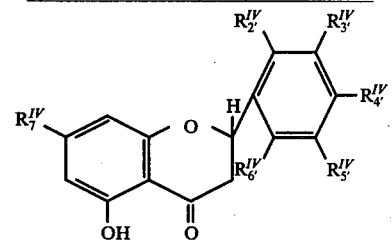

| $R_7^{IV}$ | $R_{2'}^{IV}$ | $R_{3'}^{IV}$ | $R_{4'}^{IV}$ | $R_{5'}^{IV}$ | $R_{6'}^{IV}$ | Natural | Synthetic |
|---|---|---|---|---|---|---|---|
| H | H | H | OH | H | H | | + |
| H | H | OCH$_3$ | OH | H | H | | + |
| OH | H | H | H | H | H | pinocembrin | |
| OH | H | H | OH | H | H | naringenin | |
| OH | H | H | OCH$_3$ | H | H | isosakuranetin | |
| OH | H | OCH$_3$ | OCH$_3$ | H | H | | + |
| OH | H | OCH$_3$ | OH | H | H | homoeriodictyol | |
| OH | H | OH | OCH$_3$ | H | H | hesperetin | |
| OH | OCH$_3$ | H | H | H | H | citronetin | |
| OH | OCH$_3$ | H | OCH$_3$ | H | H | | + |
| OH | OCH$_3$ | H | OCH$_3$ | H | OCH$_3$ | | + |
| OH | H | OCH$_3$ | OCH$_3$ | OCH$_3$ | H | | + |
| OH | OCH$_3$ | H | OCH$_3$ | OCH$_3$ | H | | + |
| OH | OCH$_3$ | OCH$_3$ | OCH$_3$ | H | H | | + |
| OCH$_3$ | H | H | OH | H | H | sakuranetin | | wherein $R_{6,8,3',5'}^{III}$ are substituents selected from the group consisting of H, OCOR and lower alkoxy, $R_{2'}^{III}$ and $R_{6'}^{III}$ are substituents selected from the group consisting of H and lower alkoxy and R is a substituent selected from the group consisting of lower alkyl and phenyl. As will be later explained in greater detail, for the successful reduction of acylated flavanones to flavans, according to one embodiment of the invention, it is believed necessary that the flavanones contain an acyloxy group at the 5 position, as shown. Certain other restrictions, not necessary for preparing flavan intermediates but important in converting acylated flavanones to the ultimate 3-deoxyanthocyanidins according to another embodiment of the invention, also will become apparent hereinafter.

Experimentation has shown that the highest flavan yields are obtained where the acylated flavanone is an acetylated flavanone (when R is CH$_3$). While other acyl groups (R is other lower alkyl or phenyl) may be operative, for convenience of illustration, the preferred embodiment wherein R is CH$_3$ will serve throughout the description as the primary exemplification. In this case the generic acyl designation of OCOR will be replaced by OAc, Ac standing for COCH$_3$. Further, acetoxy often will be used instead of the more generic acyloxy.

The described acylated flavanones may be conveniently prepared by conventional techniques for acylation of corresponding flavanones IV. Although almost any corresponding flavanone within the above structural limitations may be employed, those listed in Table 1, especially those of natural origin, are considered The most preferred flavanones for acylation are those derived from low-cost, abundant agrochemicals, such as hesperetin IV$_a$ and naringenin IV$_b$ (subscripts "a" and "b" will be used hereinafter to designate hesperetin and naringenin, respectively, and their respective reaction products) which, after acetylation, are converted to the triacetates III$_a$ and III$_b$:

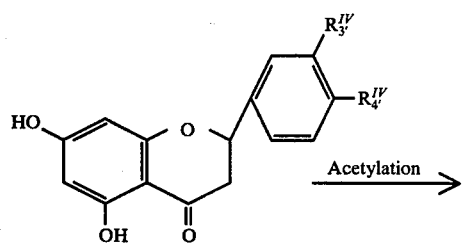

IV

IV$_a$: $R_{3'}^{IV}$ = OH; $R_{4'}^{IV}$ = OCH$_3$

IV$_b$: $R_{3'}^{IV}$ = H; $R_{4'}^{IV}$ = OH

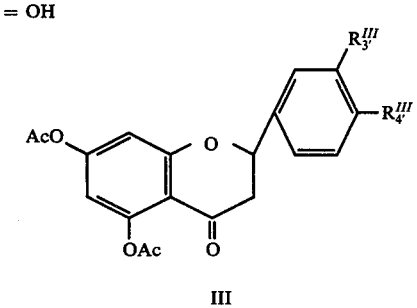

III

-continued $III_a$: $R_{3'}^{III} = OAc$; $R_{4'}^{III} = OCH_3$ $III_b$: $R_{3'}^{III} = H$; $R_{4'}^{III} = OAc$ The first step in the invention involves the reduction of the aforementioned acylated flavanones to form corresponding novel flavan intermediates of the formula:

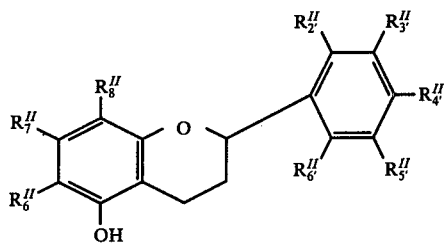
II wherein $R_{6-8,2'-6'}^{II}$ are the same as $R_{6-8,2'-6'}^{III}$ of the acylated flavanone. Additional substitutional restrictions, as will be later pointed out, must be imposed if the flavan is subsequently to be oxidized to the anthocyanidin according to a further embodiment of the invention.

Chemical reduction of flavanones to flavans is generally known. For example, reduction has been attempted by using lithium aluminum hydride and by catalytic hydrogenation with palladium. M. M. Bokadia, B. R. Brown, D. Cobern, A. Roberts and G. A. Somerfield, *J. Chem. Soc.* 1962, 1958 and D. G. Roux, *Biochem. J.* 87, 435 (1963). In both cases, unless carefully controlled, the reduction does not stop at the flavan, but proceeds further through ring hydrogenolysis to yield mainly the corresponding 1,3-diphenyl propane derivatives. This tendency towards ring cleavage is particularly severe with flavanones containing 4'—OH groups (with or without 5—OH groups).

A better way of achieving flavanone to flavan conversions is the Clemmensen reduction. A. Robertson, V. Venkateswarlu and W. B. Whalley, *J. Chem. Soc.* 3137 (1954). Although proceeding in good yields, the use of highly toxic mercury precludes the application of this method to the industrial synthesis of food grade additives.

Another prior art process makes use of sodium borohydride as the reducing agent. This reagent is reacted with hydroxyflavanones (not acylated), either in the free phenolic or methyl ether form, to yield corresponding 4-flavanols, without ring cleavage. J. Masquelier and J. Michaud, U.S. Pat. No. 3,549,661 (Dec. 22, 1970).

The reduction step of the invention, on the other hand, centers around the discovery that the reduction of, e.g., flavanone acetates $III_a$ and $III_b$ with an alkali borohydride proceeds in a different manner to yield the corresponding flavans II instead of the aforesaid 4-flavanols; i.e., the oxygen function at the 4 position is completely eliminated:

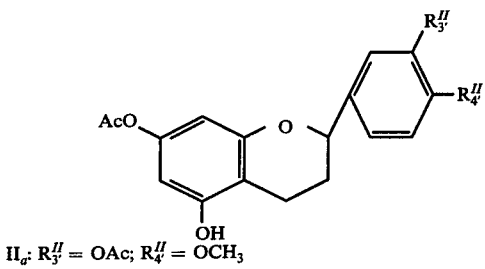

$II_a$: $R_{3'}^{II} = OAc$; $R_{4'}^{II} = OCH_3$ $II_b$: $R_{3'}^{II} = H$; $R_{4'}^{II} = OAc$

Preferably, the reduction is carried out in a suitable solvent medium. Appropriate solvents include organic solvents, especially aliphatic alcohols, alicyclic alcohols, lower aliphatic ethers, cyclic ethers and mixtures thereof. However, it must be appreciated that other solvents within the skill of the art may be used. Water also may be present.

Alkali borohydrides are considered generally effective as the reducing agent of this embodiment of the invention. While preferred results have been realized with sodium borohydride, usage of other borohydrides, e.g. lithium and potassium borohydrides, may also be acceptable.

Suitable temperatures of reaction are believed to fall within the range of 5°–50° C. Good results have been obtained when the reduction is carried out at room temperature for about 1 hour.

The inventors have found that the reduction of the carbonyl group proceeds with the loss of the proximal acetyl group at the 5 position, presumably through the intermediacy of a cyclic anion that easily eliminates the acetate group from the benzylic carbon, e.g.:

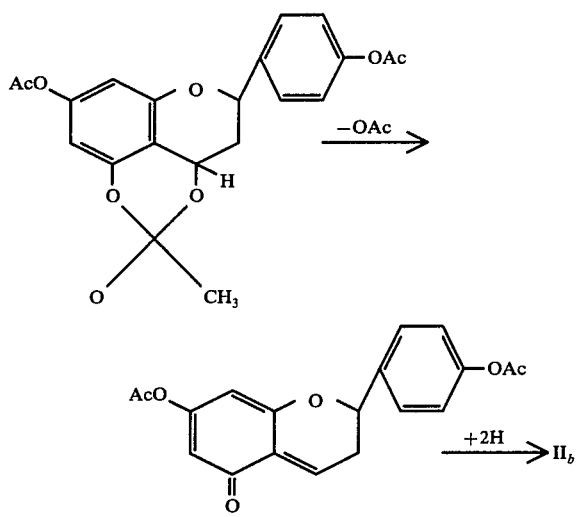

This finding constitutes an extension to flavanones of previous observations showing that o-acetoxyaromatic ketones are reduced to the corresponding o-hydroxyaromatic alkanes with sodium borohydride. B. J. McLoughlin, *Chem. Comm.* 540 (1969); K. H. Bell, *Aust. J. Chem.* 22, 601 (1969). As practiced in the present invention, it provides a novel, convenient route for the preparation of flavans derived from a 5-hydroxyflavanones.

In support of the above mechanism, it is further observed that the irreversible blocking of the phenolic group at the 5 position, or the absence of a substituent at this position, allows the reduction to proceed without elimination, yielding the 4-flavanols. For example, tetramethyl-eriodictyol gives the 4α-ol in high yield. M. S. Kamat, P. Y. Mahajan and A. B. Kulkarin, *Ind. J. Chem.* 8, 119 (1970):

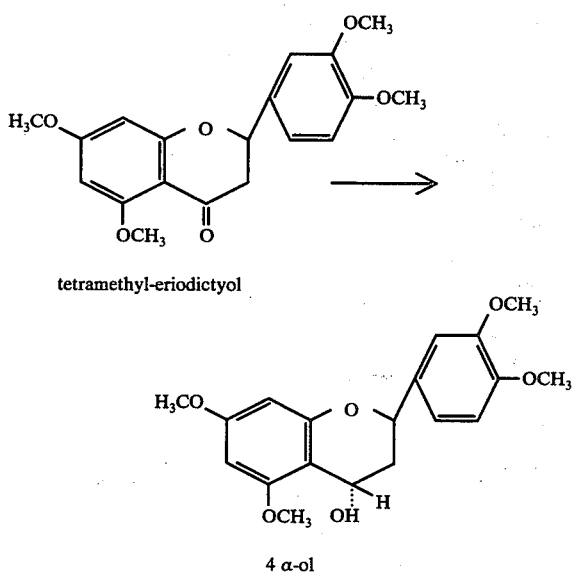

tetramethyl-eriodictyol

4 α-ol

In addition, the inventors have found that under the operative conditions exemplified in this invention, and as expected from the above mechanism, it is not possible to assist the full reduction of the carbonyl from the 7 position. For example, the reduction of 7-acetoxyflavanone with sodium borohydride gives 4,7-dihydroxyflavan in 70% yield:

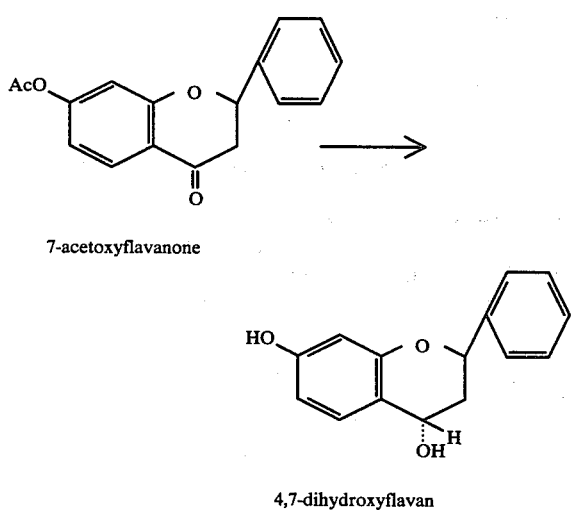

7-acetoxyflavanone 4,7-dihydroxyflavan

In a further extension of the scope of the invention, it has been discovered that the above flavan intermediates II or fully or partially acylated or hydrolyzed derivatives thereof can be oxidized to the ultimately desired 3-deoxy-anthocyanidin salts I (see below), when submitted to the action of halogenated benzoquinones in a solvent medium in the presence of a strong acid. However, a detailed study of this oxidation has revealed the need for certain structural restrictions on the flavans II, in order for the oxidation to proceed. Only when there is a free or acylated hydroxyl group either at the 4' position and/or at the 7 position is the oxidation of II to I possible. Irreversible blocking of hydroxyl groups at both positions through, e.g., methylation, or the absence of hydroxyl groups altogether as in the case of the unsubstituted flavans, makes the oxidation ineffectual. It also has been observed that flavans containing vicinal (or proximal or ortho) hydroxyl groups, either free or acylated (OH or OCOR), at the 3' and 4' positions fail to give anthocyanidins upon oxidation, presumably by over-oxidation through an ortho-quinone intermediate. This problem may be encountered with any vicinal hydroxyl and/or acyloxy groups on the B ring (see I below) and perhaps, with such vicinal groups in general, regardless of ring.

It bears mentioning that the flavans serving as the base for synthesizing the 3-deoxyanthocyanidins need not have a hydroxy or acyloxy group at the 5 position. This limitation is imposed only by the preferred technique of the invention wherein the flavans are prepared by reduction of acylated flavanones. If the flavans are derived by other known means, the substituent at the 5 position may be not only OH or OCOR but H or lower alkoxy as well.

Within this context the generic formula of the 3-deoxyanthocyanidin salts I prepared by oxidation of flavans according to the invention is:

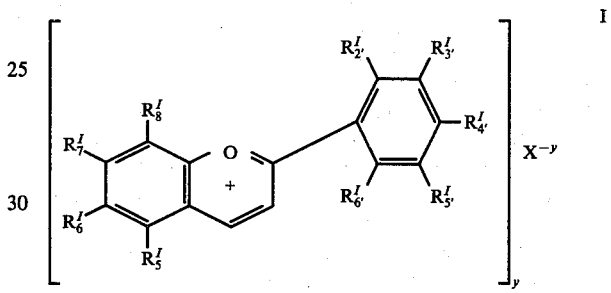

wherein $R_{5-8,2'-6'}{}^I$ are substituents selected from the group consisting of H, OH and lower alkoxy, at least one of $R_7{}^I$ and $R_4{}^I$ is OH (by appropriate acylation may be converted to OCOR), $R_{3'-5'}{}^I$ do not include vicinal OH substituents, $R_2{}^I$ and $R_6{}^I$ are substituents selected from the group consisting of H and lower alkoxy, X is an anion, and y corresponds to the valence of the anion. In a preferred embodiment $R_{5-8,2'-6'}{}^I$ do not include vicinal OH substituents. If the anthocyanidins are prepared from flavans derived by reduction of acylated flavanones III, $R_5{}^I$ is OH. As will become subsequently apparent (with reference to Table 3), best results are realized if $R_4{}^I$ is OH or lower alkoxy when $R_7{}^I$ is OH.

For hesperetin and naringenin based anthocyanidins $I_a$ and $I_b$, the structure is:

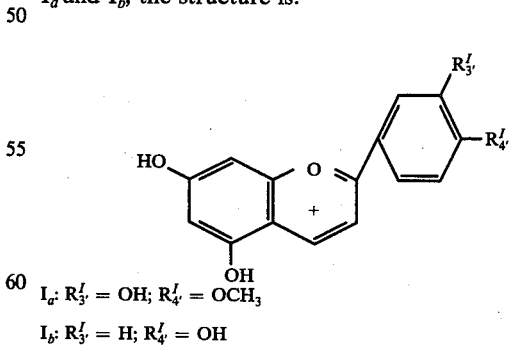

$I_a$: $R_{3'}^I$ = OH; $R_{4'}^I$ = OCH$_3$ $I_b$: $R_{3'}^I$ = H; $R_{4'}^I$ = OH

It will be appreciated that the flavan intermediates II as utilized to prepare the 3-deoxyanthocyanidins will have corresponding structural limitations as will any other precursors, such as the acylated flavanones or the flavanones prior to acylation. In other words, $R_{6-8,2'-6'}{}^{III}$ and $R_{6-8,2'-6'}{}^{II}$ will be the same as $R_{6-8,2'-6'}{}^{I}$ except for acylation substitutions.

The best apparent rationalization for the course of the oxidation is that a quinone methide intermediate is formed through phenolic oxidation at the 4' and/or 7 positions, followed by acid-catalyzed rearrangements to either the $\Delta^{2,3}$- or $\Delta^{3,4}$-flavenes which are further oxidized to 3-deoxyanthocyanidins.

Participation of flavenes in the oxidative generation of flavylium cations has been recognized before but based on the direct oxidation of nonphenolic $\Delta^{3,4}$-flavenes to flavylium cations. J. W. Clark-Lewis and D. C. Skingle, *Aust. J. Chem.* 20, 2169 (1967).

Although a wide range of conditions may be acceptable, superior results have been obtained by heating the reaction mixture up to temperatures of about 80° to 120° C. for about 0.5-2 hours.

Oxidation proceeds best in a protic medium formed by an appropriate solvent and a strong acid. In a preferred embodiment the medium includes a protic organic solvent inert to the dehydrogenative action of the halogenated benzoquinones, most suitably those belonging to the class of aliphatic monofunctional $C_2$-$C_5$ alcohols, carboxylic acids and mixtures. Glacial acetic acid has been found especially effective.

By including a strong acid and water, the necessary hydrolysis of the phenolic esters is achieved. Water may be added separately or with the acid. The acid selected should not react with the ultimate flavylium cation structure. Where the intended use of the 3-deoxyanthocyanidin requires a water soluble product, the acid preferably is one with an anion forming a water soluble anthocyanidin; otherwise, subsequent conversion to a water-soluble product is required. Obviously if a water insoluble product is permissible, a wider range of acids can be tolerated. In the case of food and/or beverage usage, the acid may have an anion not acceptable for food use but this requires a subsequent conversion step; therefore, it is preferable to select at the outset an acid acceptable for use in foods. Acceptable acids having anions forming water soluble anthocyanidins include hydrochloric, hydrobromic, sulfuric, phosphoric, hydrofluoric and aryl and alkyl sulfonic acids and mixtures. Phosphoric and hydrochloric acids are considered the best alternatives for food use, with the latter having been found particularly suitable.

Although for convenience of illustration, oxidation and hydrolysis have been described as a single step, one skilled in the art will appreciate that hydrolysis may be a separate step preceding oxidation. Further, where oxidation and hydrolysis proceed in a single step, the flavan intermediate may be fully acylated prior to the step. Interestingly, experimentation suggests that this latter approach may offer enhanced anthocyanidin yields.

Table 2 illustrates the effect of benzoquinone structure on anthocyanidin yields for oxidations of 4',5,7-triacetoxyflavan under the conditions of the present invention. The results, listed according to the increasing electron potential of the quinones, indicate that the highest apigeninidin yields are secured with the very preferred oxidants chloranil and bromanil (tetrachloro-p-benzoquinone and tetrabromo-p-benzoquinone, respectively).

TABLE 2

Relative Effectiveness of Selected Benzoquinones for the Oxidation of 4',5,7-Triacetoxyflavan (fully acetylated $II_b$) to Apigeninidin $(I_b)^a$

| Benzoquinones (arranged by increasing electron acceptor potential) | Apigeninidin yield (%)[b] |
|---|---|
| p-Benzoquinone | 0[c] |
| Tetrafluoro-p-benzoquinone | 7 |
| Tetrachloro-p-benzoquinone (Chloranil) | 30 |
| Tetrabromo-p-benzoquinone (Bromanil) | 27 |
| Tetrachloro-o-benzoquinone (o-Chloranil) | 6 |
| Tetrabromo-o-benzoquinone (o-Bromanil) | 4 |
| Dicyano-dichloro-p-benzoquinone (DDQ) | 0[d] |

[a]Oxidations with 10 mg fully acetylated $II_b$ and 15 mg quinone, in 1 ml acetic acid, plus 0.1 ml 6N HCl and 0.4 ml water, at 100° C for 1 hr.
[b]By UV analysis of purified product, using $E_{1\%\ (476\ nm)}$ = 1000 for pure apigeninidin.
[c]No apparent change in color noticed.
[d]Reaction carried out at 25° C for 30 minutes (in view of a higher reactivity of the oxidant), with deep brown color formation. Although the reaction went to completion, apigeninidin could not be isolated from the reaction mixture.

Table 3 shows in turn the importance of flavan structure on oxidations with chloranil under the conditions described in Table 2. The importance of the OH group at the 4' position is demonstrated, as well as the alternative role of the OH group at the 7 position when the 4'—OH group is blocked by methylation.

TABLE 3

Oxidation of Selected Flavans with Chloranil in AcOH/HCl (100° C, 1 hr.)

| Flavan | Anthocyanidin yield (%) |
|---|---|
| 4'-Acetoxyflavan | 48 |
| 7-Acetoxyflavan | 5 |
| 4',5,7-Triacetoxyflavan | 30 |
| 4'-Methoxy-3',5,7-triacetoxyflavan | 20 |

When the same reactions were repeated under the conditions most frequently adopted for the practice of dehydrogenation with benzoquinones, i.e., by using the most reactive DDQ in an aprotic solvent like benzene [D. Walker and J. D. Hiebert, *Chem. Rev.* 67, 153 (1967)] a very low yield of anthocyanidin was observed as a result of over-oxidation, as shown in Table 4.

TABLE 4

Oxidation of Selected Flavans with DDQ in Benzene (reflux, 2 hr.)

| Flavan | Anthocyanidin yield (%) |
|---|---|
| 4'-Hydroxyflavan | 1 |
| 7-Hydroxyflavan | 3 |
| 4',5,7-Trihydroxyflavan | 0 |
| 4'-Methoxy-3',5,7-trihydroxyflavan | 1 |

The following examples of various embodiments are presented to further illustrate and exemplify the invention.

EXAMPLE 1

4',5,7-Triacetoxyflavan

To a solution of 5.0 grams triacetylnaringenin in a mixture of 125 ml tetrahydrofuran and 125 ml ethanol was added 500 mg sodium borohydride. After stirring at room temperature for 30 minutes, an additional 500 mg $NaBH_4$ was added and stirring continued for a total of one hour. The solution was then poured into 750 ml of cold 0.5% acetic acid and extracted three times with 250 ml chloroform. Drying ($Na_2SO_4$) and evaporating the $CHCl_3$ gave a light yellow oil.

The oil was dissolved in 25 ml acetic anhydride and 30 ml pyridine and allowed to stand at room temperature overnight. It was then poured into 200 ml ice water and extracted with 150 ml CHCl$_3$. The CHCl$_3$ layer was washed with 200 ml ice water, 200 ml cold 3% HCl and 200 ml cold 0.5% NaHCO$_3$. Drying and evaporating the CHCl$_3$ again gave a pale yellow oil. This oil was separated into its two components by chromatography on a 2.5 × 40 cm. column of SILICAR CC-7 (SILICAR is a trademark for silica gel sold by Mallinckrodt) using 50% CHCl$_3$-hexane as eluant.

The fractions containing the component of higher Rf were combined and crystallized from MeOH to give 2.77 g (57% yield); two crops) of 4',5,7-triacetoxyflavan, m.p. 102°-3° C.

Anal. Calc. for C$_{21}$H$_{20}$O$_7$ : C = 65.63, H = 5.20. Found: C = 65.78, H = 5.09.

MS m/e (rel. int.) 384(18), 342(18), 300(19), 258(25), 120(38), 69(21), 43(100).

NMR δ(CDCl$_3$) 1.7-2.1 (2H, C3-H, m.), 2.20 (3H, OAc, s), 2.24 (6H, OAc, s), 2.5 - 2.7 (2H, C4-H, m.), 4.96 (1H, C2-H, q.), 6.50 (2H, C6 & C8-H, q.), 7.20 (4H, C2', 3', 5', 6'-H, q.).

IR μ (KBr) 5.65, 7.27, 8.22, 8.89, 9.24, 9.40, 9.79.

EXAMPLE 2

Apigeninidin chloride via chloranil oxidation

A mixture of 500 mg 4', 5,7-triacetoxyflavan, 750 mg chloranil, 25 ml acetic acid, 5 ml H$_2$O and 1.5 ml 6 N HCl was heated with stirring at 100° for 1 hour. After cooling in ice, the solution was diluted to 250 ml with 0.01 N HCl in MeOH and passed through a 4.5 × 10 cm column of acid-treated POLYCAR AT[1] (slurry packed) (POLYCLAR AT is a trademark for polyvinylpyrollidine sold by G.A.F.). The column was washed with a second 250 ml of 0.01 N HCl in methanol and the combined eluants concentrated on a rotary evaporator to 25 ml. This solution was then freeze dried to give a red-orange solid. After washing twice with 10 ml ethyl acetate to remove unreacted chloranil, there was obtained 144 mg (36% yield) of crude apigeninidin chloride (E$_{1\% (476\ nm)}$ = 840). A sample of purified material recrystallized from EtOH-4 N CHI had E$_{1\% (476\ nm)}$ = 1010 and was identical by IR (KBr) and TLC (cellulose) comparison with an authentic sample prepared by Robinson's procedure [2]; the yield of purified material was 30%.

UV (C$_{15}$H$_{14}$O$_4$Cl . H$_2$O; 0.01 N HCl in MeOH) λ$_{max}$ (logε): 240(3.98), 277(4.25), 324(3.66), 475(4.51).

[1] R. E. Wrolctad and B. J. Struthers, J. Chromat., 55. 405 (1971).
[2] G. M. Robinson, R. Robinson and A. R. Todd, J. Chem. Soc., 809, 1934.

EXAMPLE 3

Apigeninidin chloride via bromanil oxidation

A mixture of 500 mg 4',5,7-triacetoxyflavan, 1.2 g bromanil, 25 ml acetic acid, 5 ml water and 1.5 ml 6 N HCl was heated at 100° with stirring for 1 hour. Upon cooling, the solution was diluted to 200 ml with 0.01 N HCl in MeOh and then filtered through a pad of 30 g CELITE (a trademark for diatomaceous earth sold by Johns-Manville) mixed with 15 grams acid-treated POLYCLAR AT. The pad was washed with an additional 100 ml of 0.01 N HCl in MeOH and the combined filtrate concentrated to 25 ml on a rotary evaporator. This solution was then freeze-dried to give a red-orange solid. After washing twice with 5 ml ethyl acetate, there was obtained 126 mg (33% yield) of crude apingenininidin chloride (E$_{1\% (476\ nm)}$ = 770).

The sample was further washed five times with 5 ml ethyl ether, and then recrystallized from EtOH-4 N HCl and had E$_{1\% (476\ nm)}$ = 940. This sample was identical by infrared comparison with authentic apigeninidin chloride prepared by Robinson's procedure.

EXAMPLE 4

4'-Methoxy-3',5,7-triacetoxyflavan

To a solution of 5.0 grams triacetylhesperetin in 250 ml of 50-50 tetrahydrofuran-ethanol was added 500 mg NaBH$_4$. After stirring at room temperature for 30 minutes, an additional 500 mg NaBH$_4$ was added and stirring continued for a total of one hour. The solution was poured into 750 ml cold 0.5% acetic acid and extracted three times with 250 ml CHCl$_3$. Drying (Na$_2$SO$_4$) and evaporating the CHCl$_3$ gave a light brown oil. The oil was dissolved in 25 ml acetic anhydride and 30 ml pyridine and allowed to stand at room temperature overnight.

The solution was then poured into 200 ml ice water and extracted with 150 ml CHCl$_3$. The CHCl$_3$ layer was washed with 200 ml ice water, 200 ml cold 3% HCl and 200 ml cold 0.5% NaHCO$_3$. Drying and evaporating the CHCl$_3$ gave a pale yellow oil.

The oil was chromatographed on a 2.5 × 40 cm. column of SILICAR CC-7 using 50-50 hexane-CHCl$_3$ as eluant.

The fractions containing the component of higher Rf were combined and allowed to stand in 20 ml MeOH at 5° C overnight. The resulting white solid was removed by filtration and dried in vacuo to give 2.12 g (44% yield of 4'-methoxy-3',5,7-triacetoxyflavan, m.p. 106°-7° C.

Anal. Calc. for C$_{22}$H$_{22}$O$_8$ : C = 63.77, H = 5.31. Found: C = 63.70, H = 5.15.

MS m/e (rel. int.) 372(100), 150(85), 330(49), 43(49), 414(45), 288(40), 287(39).

NMR δ (CDCl$_3$) 2.0-2.4 (2H, C3-H, m.), 2.6-3.0 (2H, C4-H, m.), 2.32 (3H, OAc, s), 2.36 (3H, OAc, s), 2.38 (3H, OAc, s), 4.00 (3H, OCH$_3$, s), 5.10 (1H, C2-H, q.), 6.85 (2H, C6 & C8-H, q.), 7.2-7.6 (3H, C2', 5', 6'-H, m.).

IR μ (KBr) 8.26, 8.86, 5.63, 9.77, 7.27, 7.82, 9.41.

EXAMPLE 5

4'-Methylluteolinidin chloride via chloranil oxidation

A mixture of 500 mg 4'-methoxy-3',5,7-triacetoxyflavan, 700 mg chloranil, 25 ml acetic acid, 5 ml H$_2$O and 1.5 ml of 6 N HCl was heated at 100° for 1 hour with stirring. The solution was then cooled in ice and diluted with 200 ml of 0.01 N HCl in MeOH. This solution was filtered through a pad of 30 g CELITE mixed with 15 g acid-treated POLYCLAR AT [1] (see Example 2). The pad was washed with an additional 200 ml 0.01 N HCl in MeOH and the combined filtrates concentrated on a rotary evaporator to ~ 25 ml. After freeze drying, the residue was triturated with two 10 ml aliquots EtOAc followed by 15 ml of 4 N HCl to give a red-orange solid. After drying in vacuo, there was obtained 92 mg (22% yield) of 4'-methylluteolinidin chloride (E$_{1\% (490\ nm)}$ = 710).

A sample was further purified by chromatography on a 10 × 25 cm column of POLYCLAR AT using 0.01 N HCl in MeOH as eluant. The anthocyanin band was concentrated in vacuo and triturated with EtOAc to again give a red-orange solid (E$_{1\% (490\ nm)}$ = 945).

UV ($C_{15}H_{16}O_5Cl \cdot H_2O$; 0.10 N HCl in MeOH) $\lambda_{max}$ (logε): 240(4.11), 279(4.26), 320(3.58), 488(4.51).

IRμ(KBr): 8.06(8.05); 7.82(7.86); 7.41(7.43); 6.57, 6.42(6.44); 6.06(6.07) and 2.91(2.89).

IR values in parenthesis are the strongest peaks in apigeninidin chloride.

EXAMPLE 6

3',4',5,7-Tetraacetoxyflavan

To a stirred solution of 1.0 grams 3',4',5,7-tetraacetoxyflavanone in 50 ml of 50% THF-ethanol was added 100 mg $NaBH_4$. After 30 min., an additional 100 mg $NaBH_4$ was added and stirring continued at room temperature for a total of 1 hour. The mixture was then poured into 200 ml of cold 0.5% acetic acid and extracted three times with 75 ml $CHCl_3$. The combined $CHCl_3$ extracts were dried ($NA_2SO_4$) and evaporated to give a thick oil. To the oil was added 6 ml acetic anhydride and 8 ml pyridine and this solution allowed to stand at room temperature overnight. After pouring into 100 ml ice water, the resulting emulsion was extracted with 125 ml chloroform and the chloroform washed with 100 ml ice water, 100 ml cold 3% HCl and 100 ml 0.5% $NaHCO_3$. Drying ($Na_2SO_4$) and evaporating the $CHCl_3$ gave an oil which was purified by chromatography on a 2.5 × 4.0 cm column of SILICAR CC-7. The first material to elute with 60% $CHCl_3$-hexane was 3',4',5,7-tetraacetoxyflavan, which after recrystallization from MeOH, was obtained in an amount of 345 mg (36% yield) mp 143°–4° C.

ANAL. Calc. for $C_{23}H_{22}O_9$: C = 62.44, H = 4.98. Found: C = 62.44, H = 5.01.

MS m/e (rel. int.) 442(29), 400(52), 358(100), 316(85), 274(46), 139(48), 136(62), 43(84).

NMR δ($CDCl_3$) 2.1 (2H,C3-H,b.m.), 2.30 (12H,OAc,s.), 2.6 (2H,C4-H,m.), 5.0 (1H,C2-H,q.), 6.58 (2H,C6 & C8-H,q.), 7.3 (3H,C2',5',6'-H,m.).

IR μ (KBr) 2.88, 5.63, 7.27, 8.22, 8.88, 9.25, 9.80.

EXAMPLE 7

Attempted chloranil oxidation of 3',4',5,7-tetraacetoxyflavan to luteolinidin A solution of 10 mg 3',4',5,7-tetraacetoxyflavan and 15 mg chloranil in a mixture of 1 ml acetic acid, 0.4 ml H O and 0.1 ml 6N HCl was heated at 100° for 1 hr. After cooling to room temperature, the mixture was diluted to 10 ml with 0.01 N HCl in MeOH and chromatographed in a 4.5 × 10 cm column of acid-treated POLYCLAR AT using 0.01 N HCl in MeOH as eluant. As luteolinidin and apigeninidin show similar chromatographic behavior [3], any luteolinidin formed would have eluted under these conditions. No yellow anthocyanin band, however, was obtained. The brown material formed in the reaction remained adhered to the top of the column.

[3] W. K. Nip and E. E. Burns, Cereal Chem., 48, 74 (1971).

From the foregoing description, it will be apparent that changes in the process, steps or order of steps as described herein may occur to persons skilled in the art without departing from the scope and spirit of the invention. Accordingly, the foregoing description is considered to be only exemplary of the invention as defined in the appended claims.

We claim:

1. A method for preparing a 3-deoxyanthocyanidin salt of the formula:

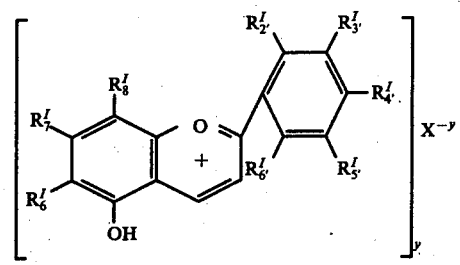

wherein $R_{6\text{-}8,3'\text{-}5'}^I$ are substituents selected from the group consisting of H, non-vicinal OH and lower alkoxy, at least one of $R_7^I$ and $R_4^I$ is OH, $R_2^I$ and $R_6^I$ are substituents selected from the group consisting of H and lower alkoxy, X is an anion and y corresponds to the valence of the anion, from an acylated flavanone of the formula:

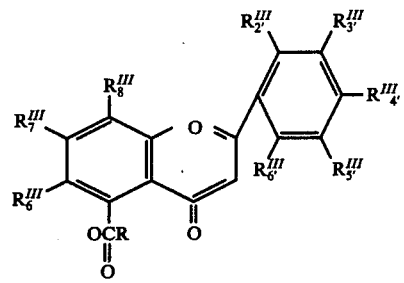

wherein $R_{6\text{-}8,2'\text{-}6'}^{III}$ are the same as $R_{6\text{-}8,2'\text{-}6'}^I$ except that those $R_{6\text{-}8,3'\text{-}5'}^{III}$ corresponding to those $R_{6\text{-}8,3'\text{-}5'}^I$ which are OH are

and is selected from the group consisting of lower alkyl and phenyl, said method comprising:
   (a) reducing said acrylated flavanone in an organic solvent medium by reaction with an alkali borohydride to form a flavan not having a 4-OH substituent and
   (b) oxidizing said flavan or an acylated or hydrolyzed derivative thereof in a solvent medium by reaction with a halogenated benzoquinone in the presence of a strong acid to form said 3-deoxyanthocyanidin salt, said solvent medium of this step and said strong acid together forming an aqueous protic medium.

2. A method according to claim 1 wherein $R_{6,8,5',6'}^I$ are H.

3. A method according to claim 1 wherein $R_7^I$ is OH.

4. A method according to claim 3 wherein $R_4^I$ is OH or lower alkoxy.

5. A method according to claim 1 wherein $R_4^I$ is OH.

6. A method according to claim 1 wherein R is a lower alkyl.

7. A method according to claim 6 wherein said acylated flavanone is an acetylated flavanone.

8. A method according to claim 7 wherein said acetylated flavanone is a fully acetylated flavanone selected from the group consisting of pinocembrin, naringenin, isosakuranetin, homoeriodictyol, hesperetin, citronetin and sakuranetin.

9. A method according to claim 8 wherein said acetylated flavanone is naringenin triacetate.

10. A method according to claim 8 wherein said acetylated flavanone is hesperetin triacetate.

11. A method according to claim 1 wherein X is an anion selected from the group consisting of chloride, bromide, sulfate, phosphate, aryl and alkyl sulfonates and fluoride.

12. A method according to claim 11 wherein X is an anion selected from the group consisting of chloride and phosphate.

13. A method according to claim 1 wherein the organic solvent of step (a) is selected from the group consisting of aliphatic alcohols, alicyclic alcohols, lower aliphatic ethers, cyclic ethers and mixtures thereof.

14. A method according to claim 1 wherein said alkali borohydride is selected from the group consisting of sodium, lithium and potassium borohydrides and mixtures thereof.

15. A method according to claim 14 wherein said alkali borohydride is sodium borohydride.

16. A method according to claim 1 wherein the solvent medium of step (b) contains a protic organic solvent inert to the dehydrogenative action of the halogenated benzoquinone.

17. A method according to claim 16 wherein the protic organic solvent of step (b) is selected from the group consisting of lower aliphatic monofunctional alcohols, carboxylic acids and mixtures thereof.

18. A method according to claim 17 wherein the protic organic solvent of step (b) is acetic acid.

19. A method according to claim 1 wherein said strong acid has the formula $H_yX$ and is selected from those acids which neither react with the anthocyanidin cation nor precipitate the same in an aqueous medium.

20. A method according to claim 1 wherein said strong acid is selected from the group consisting of hydrochloric acid, hydrobromic acid, sulfuric acid, phosphoric acid, aryl and alkyl sulfonic acids, hydrofluoric acid and mixtures thereof.

21. A method according to claim 20 wherein said strong acid is selected from the group of hydrochloric acid and phosphoric acid.

22. A method according to claim 21 wherein said strong acid is hydrochloric acid.

23. A method according to claim 1 wherein said halogenated benzoquinone is selected from the group consisting of tetrachloro-, tetrabromo- and tetrafluorobenzoquinones and mixtures thereof.

24. A method according to claim 23 wherein said halogenated benzoquinone is selected from the group consisting of tetrachloro-p-benzoquinone and tetrabromo-p-benzoquinone and mixtures thereof.

25. A method according to claim 1 wherein step (a) is carried out at a temperature of 5°–50° C. and step (b) is carried out at a temperature of about 80°–120° C. for about 0.5–2 hours.

26. A method for preparing a 3-deoxyanthocyanidin salt of the formula:

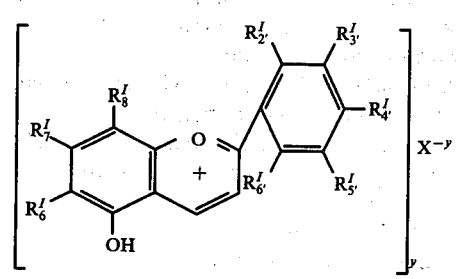

wherein $R_{6-8,3'-5'}{}^I$ are substituents selected from the group consisting of H, non-vicinal OH and lower alkoxy; at least one of $R_7{}^I$ and $R_4{}^I$ is OH and, when $R_7{}^I$ is OH, $R_4{}^I$ is OH or lower alkoxy; $R_2{}^I$ and $R_6{}^I$ are substituents selected from the group consisting of H and lower alkoxy; X is an anion selected from the group consisting of chloride, phosphate and bromide; and y corresponds to the valence of the anion, from an acetylated flavanone of the formula:

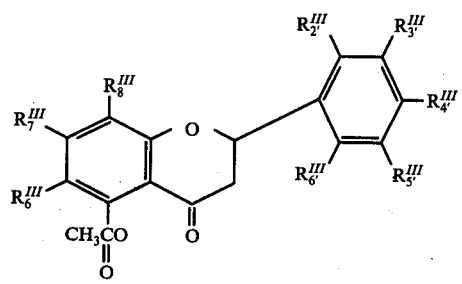

wherein $R_{6-8,2'-6'}{}^{III}$ are the same as $R_{6-8,2'-6'}{}^I$ except that those $R_{6-8,3'-5'}{}^{III}$ corresponding to those $R_{6-8,3'-5'}{}^I$ which are OH are

said method comprising:
(a) reducing said acetylated flavanone in an organic solvent medium by reaction with an alkali borohydride to form a flavan not having a 4-OH substituent, and
(b) oxidizing said flavan or an acetylated or hydrolyzed derivative thereof in a protic organic solvent medium by reaction with a halogenated benzoquinone selected from the group consisting of tetrachloro-p-benzoquinone and tetrabromo-p-benzoquinone in the presence of a strong acid and water to form said 3-deoxyanthocyanidin salt.

27. A method according to claim 26 wherein said strong acid is an acid selected from the group consisting of hydrochloric acid, phosphoric acid, hydrobromic acid and mixtures thereof.

28. A method according to claim 27 wherein said strong acid is selected from the group consisting of hydrochloric acid, phosphoric acid and mixtures thereof.

29. A method according to claim 26 wherein said strong acid is hydrochloric acid.

30. A method according to claim 29 wherein $R_{6,8,5',6'}{}^I$ are H.

31. A method according to claim 30 wherein said acetylated flavanone is a fully acetylated flavanone selected from the group consisting of pinocembrin, naringenin, isosakuranetin, homoeriodictyol, hesperetin, citronetin and sakuranetin.

32. A method according to claim 31 wherein said acetylated flavanone is naringenin triacetate.

33. A method according to claim 31 wherein said acetylated flavanone is hesperetin triacetate.

34. A method according to claim 31 wherein said alkali borohydride is selected from the group consisting of sodium, lithium and potassium borohydrides.

35. A method according to claim 34 wherein said alkali borohydride is sodium borohydride.

36. A method for preparing a 3-deoxyanthocyanidin said of the formula:

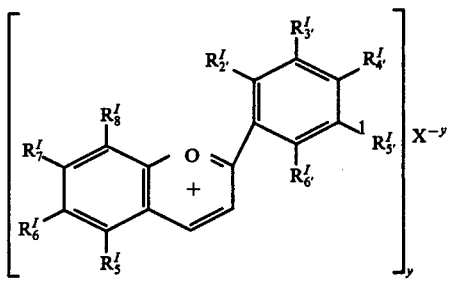

wherein $R_{5-8,3'-5'}{}^I$ are substituents selected from a group consisting of H, non-vicinal OH and lower alkoxy, at least one of $R_7{}^I$ and $R_4{}^I$ is OH, $R_2{}^I$ and $R_6{}^I$ are substituents selected from a group consisting of H and lower alkoxy, X is an anion and y corresponds to the valence of the anion from a flavan of the formula:

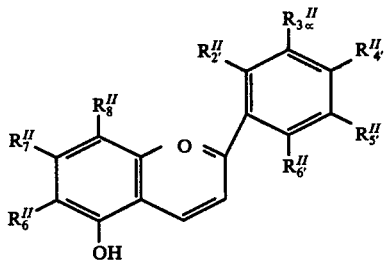

wherein $R_{5-8,2'-6'}{}^{II}$ are the same as $R_{5-8,2'-6'}{}^I$ except that those $R_{5-8,3'-5'}{}^{II}$ corresponding to those $R_{5-8,3'-5'}{}^I$ which are OH are OH or

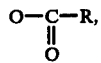

R is selected from the group consisting of lower alkyl and phenyl, said method comprising
  oxidizing said flavan in a solvent medium by reaction with a halogenated benzoquinone in the presence of a strong acid to form said 3-deoxyanthocyanidin salt, said solvent medium and said strong acid together forming an aqueous protic medium.

37. A method according to claim 36 wherein $R_5{}^I$ is OH.

38. A method according to claim 37 wherein $R_{6,8,5',6'}{}^I$ are H.

39. A method according to claim 38 wherein $R_7{}^I$ is OH.

40. A method according to claim 39 wherein $R_4{}^I$ is OH or lower alkoxy.

41. A method according to claim 40 wherein the flavan is selected from the group consisting of 4',5,7-trihydroxyflavan; 4'-methoxy-3',5,7-trihydroxyflavan and acylated derivatives thereof.

42. A method according to claim 40 wherein R is a lower alkyl.

43. A method according to claim 42 wherein said flavan is a flavan selected from the group consisting of 4',5,7-trihydroxyflavan; 4'-methoxy-3',5,7-trihydroxyflavan and acetylated derivatives thereof.

44. A method according to claim 43 wherein said flavan is 5-hydroxy-4',7-diacetoxyflavan.

45. A method according to claim 43 wherein said flavan is 5-hydroxy-4'-methoxy-3',7-diacetoxyflavan.

46. A method according to claim 42 wherein X is an anion selected from the group consisting of chloride, bromide, sulfate, phosphate, aryl and alkyl sulfonates and fluoride.

47. A method according to claim 46 wherein X is an anion selected from the group consisting of chloride and phosphate.

48. A method according to claim 47 wherein X is chloride.

49. A method according to claim 42 wherein the solvent medium contains a protic organic solvent inert to the dehydrogenative action of the halogenated benzoquinone.

50. A method according to claim 49 wherein the protic organic solvent is selected from the group consisting of lower aliphatic monofunctional alcohols, carboxylic acids and mixtures thereof.

51. A method according to claim 50 wherein the protic organic solvent is acetic acid.

52. A method according to claim 42 wherein the strong acid has the formula $H_yX$ and is selected from those aqueous acids which neither react with the anthocyanidin cation nor precipitate the same in an aqueous medium.

53. A method according to claim 52 wherein said strong acid is selected from the group consisting of hydrochloric acid, hydrobromic acid, sulfuric acid, phosphoric acid, aryl and alkyl sulfonic acids and mixtures thereof.

54. A method according to claim 42 wherein said halogenated benzoquinone is selected from the group consisting of tetrachloro-, tetrabromo- and tetrafluorobenzoquinones.

55. A method according to claim 54 wherein said halogenated benzoquinone is selected from the group consisting of tetrachloro-p-benzoquinone and tetrabromo-p-benzoquinone.

56. A method according to claim 42 wherein said oxidizing is carried out at a temperature of about 80°–120° C for about 0.5–2 hours.

* * * * *

UNITED STATES PATENT AND TRADEMARK OFFICE
CERTIFICATE OF CORRECTION

PATENT NO. : 4,105,675            Page 1 of 4

DATED : August 8, 1978

INVENTOR(S) : Guillermo A. Iacobucci, et al.

It is certified that error appears in the above-identified patent and that said Letters Patent are hereby corrected as shown below:

Column 2, line 58: Change "$R_{6-8,3'-5'}^{I}$" to --$R_{6-8,3'-5'}^{I}$--;

Column 2, line 59: Change "$R_{3'-5'}^{I}$" and "$R_{6-8}^{I}$" to --$R_{3'-5'}^{I}$-- and --$R_{6-8}^{I}$-- respectively.

Column 3, line 13: Change "$R_{6-8,2'-6'}^{III}$" to -- $R_{6-8,2'-6'}^{III}$ -- and change "$R_{6-8,2'-6'}^{I}$" to --$R_{6-8,2'-6'}^{I}$--;

Column 3, line 14: Change "$R_{6-8,3'-5'}^{III}$" to --$R_{6-8,3'-5'}^{III}$-- and change "$R_{6-8,3'-5'}^{I}$" to --$R_{6-8,3'-5'}^{I}$--;

Column 3, line 15: following "are OH are" insert --- $O-\overset{O}{\underset{}{C}}-R$ ---

Column 3, line 38: Change "$R_{6,8,5' and/or\ 6'}^{I}$" to --$R_{6,8,5' and/or 6'}^{I}$--

Column 4, line 15: Change "$R_{6-8,2'-6'}^{I}$" to --$R_{6-8,2'-6'}^{I}$--;

UNITED STATES PATENT AND TRADEMARK OFFICE
CERTIFICATE OF CORRECTION

PATENT NO. : 4,105,675            Page 2 of 4
DATED : August 8, 1978
INVENTOR(S) : Guillermo A. Iacobucci, et al.

It is certified that error appears in the above-identified patent and that said Letters Patent are hereby corrected as shown below:

Column 4, line 39: Change "$R_{6-8,3'-5'}{}^{II}$" to --$R^{II}_{6-8,3'-5'}$--.

Column 7, line 20: Change "$R_{6-8,2'-6'}{}^{II}$" to --$R^{II}_{6-8,2'-6'}$-- and change "$R_{6-8,2'-6'}{}^{III}$" to --$R^{III}_{6-8,2'-6'}$--.

Column 10, line 35: Change "$R_{5-8,2'-6'}{}^{I}$" to --$R^{I}_{5-8,2'-6'}$--;

Column 10, line 38: Change "$R_{3'-5'}{}^{I}$" to --$R^{I}_{3'-5'}$--;

Column 10, line 68: Change "$R_{6-8,2'-6'}{}^{III}$" to --$R^{III}_{6-8,2'-6'}$--.

Column 11, line 1: Change "$R_{6-8,2'-6'}{}^{II}$" to --$R^{II}_{6-8,2'-6'}$--; and change "$R_{6-8,2'-6'}{}^{I}$" to --$R^{I}_{6-8,2'-6'}$--.

UNITED STATES PATENT AND TRADEMARK OFFICE
CERTIFICATE OF CORRECTION

PATENT NO. : 4,105,675

DATED : August 8, 1978

INVENTOR(S) : Guillermo A. Iacobucci, et al.

It is certified that error appears in the above-identified patent and that said Letters Patent are hereby corrected as shown below:

Column 13, line 44:   Change "CHl" to --HCl--;

Column 13, line 61:   Change "MeOh" to --MeOH--.

Column 14, line 35:   following "Yield" insert --)--.

Column 16, lines 20-32:   that portion of the formula reading

" 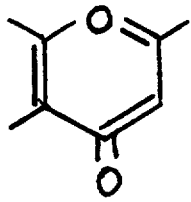 " should read -- 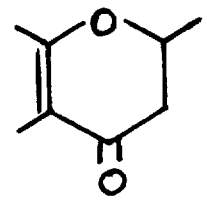 --;

UNITED STATES PATENT AND TRADEMARK OFFICE
CERTIFICATE OF CORRECTION

PATENT NO. : 4,105,675                          Page 4 of 4

DATED : August 8, 1978

INVENTOR(S) : Guillermo A. Iacobucci, et al.

It is certified that error appears in the above-identified patent and that said Letters Patent are hereby corrected as shown below:

Column 16, line 41: Following "and" insert --R--;

Column 16, line 43: Change "acrylated" to --acylated--.

Column 18, line 37: Change "Oh" to --OH--.

Column 19, lines 36-47: that portion of the structural formula reading " 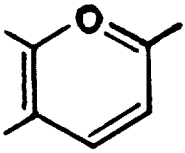 " should read -- 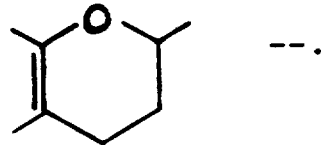 --.

Signed and Sealed this

Fifth Day of June 1979

[SEAL]

Attest:

RUTH C. MASON  
Attesting Officer

DONALD W. BANNER  
Commissioner of Patents and Trademarks